(12) United States Patent
Park et al.

(10) Patent No.: US 9,636,054 B2
(45) Date of Patent: May 2, 2017

(54) ATTENUATED TOTAL REFLECTION SPECTROSCOPIC ANALYSIS APPARATUS HAVING DEVICE FOR MEASURING SPECIMEN CONTACT AREA AND METHOD OF OPERATING THE SAME

(71) Applicant: SAMSUNG ELECTRONICS CO., LTD., Suwon-si (KR)

(72) Inventors: Sangyun Park, Hwaseong-si (KR); Sangkyu Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 148 days.

(21) Appl. No.: 14/809,433

(22) Filed: Jul. 27, 2015

(65) Prior Publication Data

US 2016/0198985 A1 Jul. 14, 2016

(30) Foreign Application Priority Data

Jan. 14, 2015 (KR) ........................ 10-2015-0006978

(51) Int. Cl.
| | |
|---|---|
| *G01N 21/55* | (2014.01) |
| *A61B 5/1455* | (2006.01) |
| *G01N 21/552* | (2014.01) |
| *A61B 5/00* | (2006.01) |

(52) U.S. Cl.
CPC ......... *A61B 5/1455* (2013.01); *G01N 21/552* (2013.01); *A61B 5/6843* (2013.01); *A61B 2562/0238* (2013.01)

(58) Field of Classification Search
CPC .. G01N 21/552; A61B 5/1455; A61B 5/6843; A61B 2562/0238; G01B 11/285

USPC ......................................................... 356/445
See application file for complete search history.

(56) References Cited

U.S. PATENT DOCUMENTS

2004/0036881 A1* 2/2004 Sharma ................ G01N 21/553
356/445
2013/0155410 A1 6/2013 Enderby et al.

FOREIGN PATENT DOCUMENTS

| JP | 11-155844 A | 6/1999 |
|---|---|---|
| JP | 2003-90793 A | 3/2003 |
| JP | 2006-329635 A | 12/2006 |
| KR | 10-2005-0074155 A | 7/2005 |

* cited by examiner

*Primary Examiner* — Kara E Geisel
*Assistant Examiner* — Amanda Merlino
(74) *Attorney, Agent, or Firm* — Sughrue Mion, PLLC

(57) ABSTRACT

An attenuated total reflection (ATR) spectroscopic analysis apparatus includes an ATR prism including: an upper surface that contacts a specimen, a lower surface facing the upper surface, a first surface that is slanted and connected to the upper surface and the lower surface, and a second surface that is slanted and connected to the upper surface and the lower surface and facing the first surface; a light source configured to emit a light towards the first surface of the ATR prism; a light receiver that is provided to face the lower surface of the ATR prism and configured to receive the light that is diffusely reflected and output from the lower surface and output an electrical signal based on the received light; and a computation processor configured to calculate a contact area of the specimen with the upper surface of the ATR prism in response to the electrical signal.

20 Claims, 7 Drawing Sheets

ATTENUATED TOTAL REFLECTION SPECTROSCOPIC ANALYSIS APPARATUS HAVING DEVICE FOR MEASURING SPECIMEN CONTACT AREA AND METHOD OF OPERATING THE SAME

CROSS-REFERENCE TO RELATED APPLICATION

This application claims the benefit of Korean Patent Application No. 10-2015-0006978, filed on Jan. 14, 2015, in the Korean Intellectual Property Office, the disclosure of which is incorporated herein in its entirety by reference.

BACKGROUND

1. Field

Exemplary embodiments relate to an attenuated total reflection spectroscopic analysis apparatus having a device for measuring a specimen contact area.

2. Description of the Related Art

An attenuated total reflection (ATR) spectroscopic analysis apparatus includes a prism (hereinafter, also referred to as a "medium 2") that contacts a medium 1 which is an object (or a specimen) to be examined. When an angle of incident light from the medium 2 to the medium 1 is greater than a critical angle, the light cannot pass through the medium 1 but is totally reflected towards the medium 2 at the interface between the medium 1 and the medium 2. At this point, a small amount of an evanescent wave extends into the medium 1. The incident light is attenuated due to the evanescent wave. The ATR spectroscopic analysis is a technique to analyze the medium 1 by measuring the attenuated light at wavelengths due to the evanescence wave in the medium 1.

In an ATR spectroscopic analysis, a contacting area between the medium 1 and the medium 2 may not be uniform, and the attenuation of light may vary according to the variation of the contact area, and thus, the measuring result may be incorrect.

When the medium 1, which is an object to be examined by using the medium 2 (an ATR prism), is a liquid, since a contact area between the ATR prism and the medium 1 is constant and is not changed, the measuring result may be correct.

However, when the medium 1 is formed in a solid phase or is a living body, the contact area between the ATR prism and the medium 1 may not be the same as a measuring area. In particular, when a bio-analysis is performed by applying the ATR spectroscopic analysis apparatus on a surface of a living body, a contact area between the medium 1 and the medium 2 may vary according to the roughness of skin, the degree of hydration, or pressure pressing on the skin, and thus, the measuring result may not be correct.

SUMMARY

Provided is an attenuated total reflection (ATR) spectroscopic analysis apparatus having a device for measuring a contact area of a specimen (e.g., a living body) that is in contact with an ATR prism and a method of operating the apparatus.

Additional aspects will be set forth in part in the description which follows and, in part, will be apparent from the description, or may be learned by practice of the presented exemplary embodiments.

According to an aspect of an exemplary embodiment, an attenuated total reflection (ATR) spectroscopic analysis apparatus includes an ATR prism including an upper surface that contacts a specimen, a lower surface facing the upper surface, a first surface that is slanted and connected to the upper surface and the lower surface, and a second surface that is slanted and connected to the upper surface and the lower surface and facing the first surface; a light source configured to emit a light towards the first surface of the ATR prism; a light receiver that is provided to face the lower surface of the ATR prism and configured to receive the light that is diffusely reflected and output from the lower surface and output an electrical signal based on the received light; and a computation processor configured to calculate a contact area of the specimen with the upper surface of the ATR prism in response to the electrical signal received by the light receiver.

The ATR spectroscopic analysis apparatus may further include another light source configured to emit another light towards the first surface of the ATR prism, and another light receiver configured to receive the other light that is totally internally reflected, passed through the ATR prism, and output from the second surface and output an electrical signal based on the received light, wherein the computation processor may be configured to calculate an analyte concentration of the specimen by using the electrical signal received by the another light receiver, and calculate an analyte concentration of the specimen per unit area by dividing the calculated analyte concentration with the contact area of the specimen with the ATR prism.

According to another aspect of an exemplary embodiment, an ATR spectroscopic analysis apparatus includes an ATR prism comprising an upper surface that contacts a specimen, a lower surface facing the upper surface, a first surface that is slanted and connected to the upper surface and the lower surface, and a second surface that is slanted and connected to the upper surface and the lower surface and facing the first surface; a mask that is provided on the upper surface of the ATR prism and has an opening; a light source configured to emit a light towards the first surface of the ATR prism; a light receiver configured to receive the light that is output from the second surface by being totally internally reflected and passed through the ATR prism and output an electrical signal based on the received light; and a computation processor configured to calculate a contact area of the specimen with the upper surface of the ATR prism in the opening of the mask in response to the electrical signal received from the light receiver.

The light receiver may be configured to calculate a reverse image of the contact area of the specimen by receiving the second light.

The ATR spectroscopic analysis apparatus may further include another light source configured to emit another light towards the first surface of the ATR prism, and another light receiver configured to receive the first light that is totally internally reflected, passed through the ATR prism, and output from the second surface and output an electrical signal based on the received light, and the computation processor may be configured to calculate an analyte concentration of the specimen by using the electrical signal received from the another light receiver, and calculate an area of a first region of the ATR prism that is in contact with air in the opening by using the electrical signal received by the light receiver and calculate the contact area of the specimen in the opening by subtracting the area of the first region from the area of the opening, and calculate an analyte concentration of the specimen per unit area by dividing the analyte concentration with the contact area.

The mask may be formed of germanium (Ge), silicon (Si), or tungsten (W).

According to another aspect of an exemplary embodiment, a method of operating an attenuated total reflection (ATR) spectroscopic analysis apparatus includes measuring an analyte concentration of a specimen that is in contact with a surface of an ATR prism; calculating a contact area of the specimen with the ATR prism; and calculating an analyte concentration per unit area by correcting the analyte concentration with the contact area of the specimen.

The measuring of the analyte concentration may include: contacting the specimen on the surface of the ATR prism, the surface being an upper surface; emitting a first light with a first incident angle towards a slanted first surface of the ATR prism, the slanted first surface being connected to the upper surface; detecting the first light that is totally internally reflected and output from a slanted second surface facing the slanted first surface of the ATR prism, the slanted second surface being connected to the upper surface; and calculating the analyte concentration based on an optical intensity of an evanescent wavelength of the detected first light at a region of the ATR prism that is in contact with the specimen.

The first incident angle may be greater than a first critical angle at which the first light is totally internally reflected at a region of the ATR prism that is in contact with air and a second critical angle at which the first light is totally internally reflected at a region of the ATR prism that is in contact with the specimen.

The calculating of the contact area of the specimen may include: contacting the specimen on the upper surface of the ATR prism; emitting a second light with a second incident angle towards the slanted first surface of the ATR prism; detecting the second light that is diffusely reflected and is output from a lower surface of the ATR prism facing the upper surface; and calculating the contact area of the specimen that is in contact with the ATR prism based on the detected second light.

The second incident angle may be an angle between the first critical angle and the second critical angle.

The calculating of the contact area of the specimen may include: contacting the specimen with the upper surface of the ART prism through an opening of a mask formed on the upper surface of the ATR prism; emitting the second light with a second incident angle towards the slanted first surface of the ATR prism; detecting the second light that is totally internally reflected and is output from the slanted second surface; calculating a contact area of the ATR prism that is in contact with air based on the detected second light; and calculating the contact area of the specimen that is in contact with the upper surface of the ATR prism in the opening by subtracting the contact area with air from an area of the opening.

The second incident angle may be an angle between the first critical angle and the second critical angle.

A total internal reflection critical angle of the mask may be greater than the first critical angle and the second critical angle, and the first light and the second light may generate a frustrated total internal reflection (FTIR) at an interface between the ATR prism and the mask.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
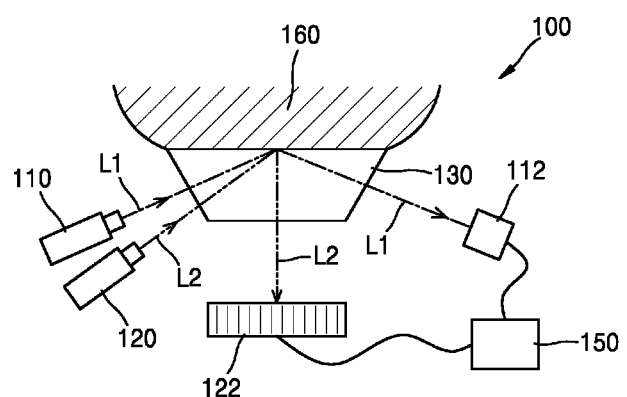
FIG. 1 is a schematic drawing of an ATR spectroscopic analysis apparatus having a device for measuring a specimen contact area, according to an exemplary embodiment.

Reference will now be made in detail to exemplary embodiments, examples of which are illustrated in the accompanying drawings. In the drawings, the thicknesses of layers and regions are exaggerated for clarity. The exemplary embodiments described below are exemplary only, and thus, may be embodied in many different forms.

It will be understood that when an element or layer is referred to as being "above" or "on" another element or layer, the element or layer may be directly on another element or layer or intervening elements or layers may be present.

It will be understood that, although the terms "first", "second", etc., may be used herein to describe various elements, these elements should not be limited by these terms. These terms are only used to distinguish one element from another element.

The singular forms include the plural forms unless the context clearly indicates otherwise. It will be understood that when a part "comprise(s)" a constituent element, the part may further include other elements unless there is a specifically contradictory element.

Also, according to an exemplary embodiment, the terms " . . . unit" or "module" denote a unit that processes at least one function or operation, and the unit may be realized as hardware or software, or a combination of hardware and software.

Hereinafter, an attenuated total reflection (ATR) spectroscopic analysis apparatus having a device for measuring a specimen contact area and a method of operating the ATR spectroscopic analysis apparatus will be described.

FIG. 1 is a schematic drawing of an ATR spectroscopic analysis apparatus 100 having a device for measuring a specimen contact area, according to an exemplary embodiment.

Referring to FIG. 1, the ATR spectroscopic analysis apparatus 100 includes a first light source 110 and a first light receiver 112 for attenuated total reflection (ATR) analysis, a second light source 120 and a second light receiver 122 for measuring a specimen contact area, and an ATR prism 130 to which light of the first light source 110 and light of the second light source 120 enter. The ATR spectroscopic analysis apparatus 100 includes a computation processing unit 150 (e.g., computation processor) that calculates a concentration of an analyte of a specimen 160 according to an actual specimen contact area by receiving an electrical signal from the first light receiver 112 and the second light receiver 122.

The first light source 110 and the second light source 120 are light sources that emit a spot light having a predetermined diameter, and in FIG. 1, the first light source 110 and the second light source 120 are depicted as point light sources for convenience.

The specimen 160 may have a solid surface. The specimen 160 may be a living body, for example, may be a portion of a human body, such as a wrist, etc.

Figure 2:
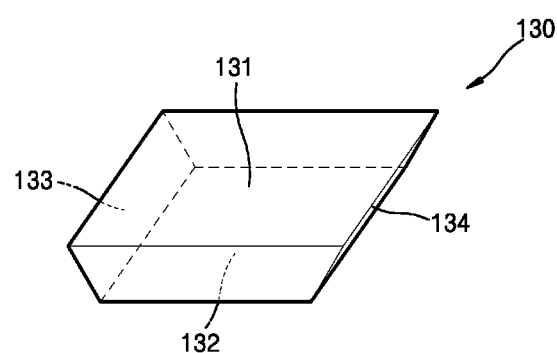
FIG. 2 is a perspective view of a structure of an ATR prism according to an exemplary embodiment.

FIG. 2 is a perspective view of a structure of the ATR prism 130 according to an exemplary embodiment.

The ATR prism 130 may be formed of zinc selenide (ZnSe), germanium (Ge), or diamond. Referring to FIG. 2, the ATR prism 130 includes an upper surface 131 that contacts the specimen 160, a lower surface 132 opposite to the upper surface 131, a first surface 133, and a second surface 134 that are inclined. The upper surface 131 has a wider area than the lower surface 132. An angle that is formed by the upper surface 131 and the first surface 133 may be approximately in a range from about 30° to about 60°.

Light incident to the first surface 133 of the ATR prism 130 with a predetermined angle is totally reflected (totally internally reflected) according to a material that contacts the upper surface 131. A critical angle that begins a total reflection is expressed as Equation 1 as below.

$$\sin \theta c = n1/n2 \qquad \text{Equation 1}$$

Here, $\theta c$ is a total reflection critical angle, n1 is a refractive index of a material that contacts the upper surface 131 of the ATR prism 130, and n2 is a refractive index of the ATR prism 130. The refractive index of the ATR prism 130 may vary according to wavelengths. For example, the ATR prism 130 formed of ZnSe may have a refractive index approximately in a range from about 2.6 to about 2.4. As the wavelength of incident light becomes longer, the refractive index of the ATR prism 130 formed of ZnSe becomes smaller.

Figure 3:
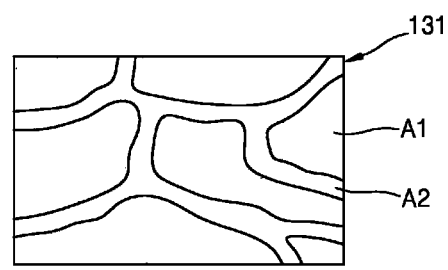
FIG. 3 is a mimic diagram showing an actual area of a specimen that is in contact with an upper surface of an ATR prism according to an exemplary embodiment.

FIG. 3 is a mimic diagram showing an actual area of a specimen that is in contact with the upper surface 131 of the ATR prism 130 according to an exemplary embodiment.

Referring to FIG. 3, a first region A1 where the specimen 160 is actually in contact with the upper surface 131 of the ATR prism 130 and a second region A2 that contacts air are depicted. If the specimen 160 is a living body, an area of the first region A1 may vary according to a pressure pressing the specimen 160 to the ATR prism 130. Accordingly, when an analyte of the specimen 160 is measured by using the first light source 110 and the first light receiver 112, the concentration of the analyte may vary according to the variable first region A1.

Figure 4:
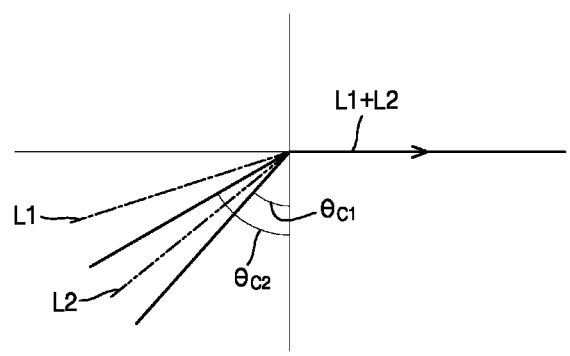
FIG. 4 is a drawing for explaining a principle of a method of operating an ATR spectroscopic analysis apparatus according to an exemplary embodiment.

FIG. 4 is a drawing for explaining a principle of a method of operating ATR spectroscopic analysis apparatus according to an exemplary embodiment.

Referring to FIG. 4, when the upper surface 131 of the ATR prism 130 is in contact with air, refractive index n1 is 1, and a first critical angle $\theta c1$ at which the total reflection begins is determined by the Equation 1.

When the upper surface 131 of the ATR prism 130 is in contact with the specimen 160, for example, the specimen 160 is a living body, the refractive index of the living body is approximately 1.87, and a second critical angle $\theta c2$ is determined by Equation 1. Since the living body has a refractive index greater than that of air, the second critical angle $\theta c2$ is greater than the first critical angle $\theta c1$.

When an incident angle of first light L1 incident to the first surface 133 of the ATR prism 130 is greater than the first critical angle $\theta c1$ and the second critical angle $\theta c2$, a total reflection occurs at a region of the upper surface 131 of the ATR prism 130 where the specimen 160 is in contact, and also, a total reflection occurs at a region of the upper surface 131 of the ATR prism 130 where the specimen 160 is not in contact, that is, the region of the upper surface 131 that contacts air.

When an incident angle of second light L2 incident to the first surface 133 of the ATR prism 130 is between the first critical angle $\theta c1$ and the second critical angle $\theta c2$, a total reflection occurs at a region of the upper surface 131 where the specimen 160 is not in contact with the ATR prism, and a total reflection does not occur at a region of the upper surface 131 where the specimen 160 is in contact with the ATR prism, and thus, a frustrated total internal reflection (FTIR) occurs. That is, a diffused reflection occurs at a region of the upper surface 131 that is in contact with air.

The first light source 110 may be a device that emits infrared light. The first light source 110 may be a light-emitting device or a laser diode that emits the first light L1 having a wavelength in a range from about 1,000 nm to about 1,500 nm. The first light source 110 irradiates the first surface 133 of the ATR prism 130 with the first light L1 having a first incident angle. The first incident angle is greater than the first critical angle $\theta c1$ and the second critical angle $\theta c2$, and accordingly, the first light L1 (also referred to as a first input light) is totally reflected at an interface between the specimen 160 and the ATR prism 130.

The first light receiver 112 may be a photodiode that detects the first light L1. The first light receiver 112 generates an electrical signal by receiving the first light L1 (also referred to as a first output light) that is totally reflected at the ATR prism 130 towards the second surface 134 of the ATR prism 130. The electrical signal detected by the first light receiver 112 is transmitted to the computation processing unit 150. The computation processing unit 150 compares the electrical signal with a wavelength spectrum of the first input light, and calculates a concentration of an analyte by computing an attenuated wavelength and its intensity in a wavelength spectrum of the first output light. This result of calculation provides an actual contact area of the specimen 160 that is actually in contact with the upper surface 131 of the ATR prism 130.

The second light source 120 may emit the second light L2 having a wavelength in a range from about 400 nm to about 750 nm. The second light source 120 may be a light-emitting device or a laser diode. The second light source 120 may be a heat light source that uses a heat generating material such as tungsten. The second light source 120 irradiates the first surface 133 of the ATR prism 130 in a second incident angle with the second light L2 (also referred to as a second input light). The second incident angle may be an angle between the first critical angle $\theta c1$ and the second critical angle $\theta c2$. Accordingly, the second light L2 is totally reflected at a region of the upper surface 131 that contacts air and is diffusively reflected at a region of the upper surface 131 that contacts the specimen 160.

The second light receiver 122 may be disposed to face the lower surface 132 of the ATR prism 130. The second light receiver 122 may be disposed on a location facing the specimen 160 with respect to the ATR prism 130. The second light receiver 122 may be an imaging device, for example, a photodiode array or a charge-couple device (CCD).

The second light receiver 122 detects the second light L2 (also referred to as a second output light) that is outputted towards the lower surface 132 of the ATR prism 130 by being diffusively reflected at the ATR prism 130. The second light receiver 122 generates an electrical signal in response to the detected second output light and transmits the electrical signal to the computation processing unit 150. The computation processing unit 150 generates a wavelength spectrum with respect to a contact area (refer to A1 of FIG. 3) at the interface between the specimen 160 and the ATR prism 130 in response to the electrical signal detected at the second light receiver 122. According to the wave spectrum, an actual contact area of the specimen 160 with the ATR prism 130 is calculated. Accordingly, a concentration of an analyte per unit area of the specimen 160 is calculated when the concentration of analyte measured at the first light receiver 112 is divided by the actual contact area.

The second light L2 is totally reflected at an interface between the specimen 160 and air. The totally reflected light enters into the first light receiver 112. Since the second light L2 has a wavelength different from that of the first light L1, the second light L2 may not be detected by the first light receiver 112. When the first light receiver 112 detects the second light L2, since the first light L1 has a different wavelength from that of the second light L2, the first light receiver 112 may selectively detect the second light L2 from the first light L1.

The device for measuring a specimen contact area measures an actual contact area of the specimen 160 by using the second light source 120 and the second light receiver 122 when measuring an analyte of the specimen 160. When the concentration of the analyte is corrected by using the measured specimen contact area, a concentration of the analyte per unit area may be obtained regardless of the variation of the contact area of the specimen 160 that is in contact with the ATR prism 130 when measuring the concentration of the analyte.

In the exemplary embodiment described above, the first light L1 and the second light L2 have different wavelengths from each other. However, the current exemplary embodiment is not limited thereto. For example, the detection may be performed such that a light source that emits the first light L1 and the second light L2 with the same wavelength is used but the first light L1 having a first incident angle and the second light L2 having a second incident angle are respectively irradiated with different timings from each other.

When the first light L1 and the second light L2 are irradiated on the second contact area A2 that is in contact with air, both the first light L1 and the second light L2 enter the first light receiver 112 from the ATR prism 130. Thus, when a concentration of an analyte is measured by optionally detecting the first light L1, the second light L2 may act as noise. Therefore, the noise may be removed by differentiating the incidence timings of the first light L1 and the second light L2.

Hereinafter, a method of measuring a specimen contact area and an operating method of an ATR spectroscopic analysis apparatus will be described with reference to the accompanying drawings.

Figure 5:
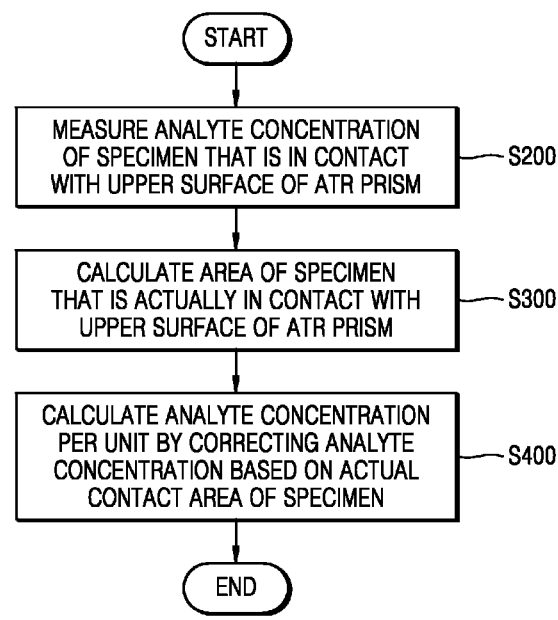
FIG. 5 is a flow chart illustrating a method of operating an ATR spectroscopic analysis apparatus according to an exemplary embodiment.

FIG. 5 is a flow chart illustrating a method of operating an ATR spectroscopic analysis apparatus according to an exemplary embodiment.

Referring to FIG. 5, an analyte concentration of the specimen 160 that is in contact with the upper surface 131 of the ATR prism 130 is measured at operation S200.

An actual contact area of the specimen 160 that is in contact with the ATR prism 130 is calculated at operation S300.

An analyte concentration per unit area is calculated by correcting the calculated analyte concentration based on the actual contact area of the specimen 160 at operation S400.

Figure 6:
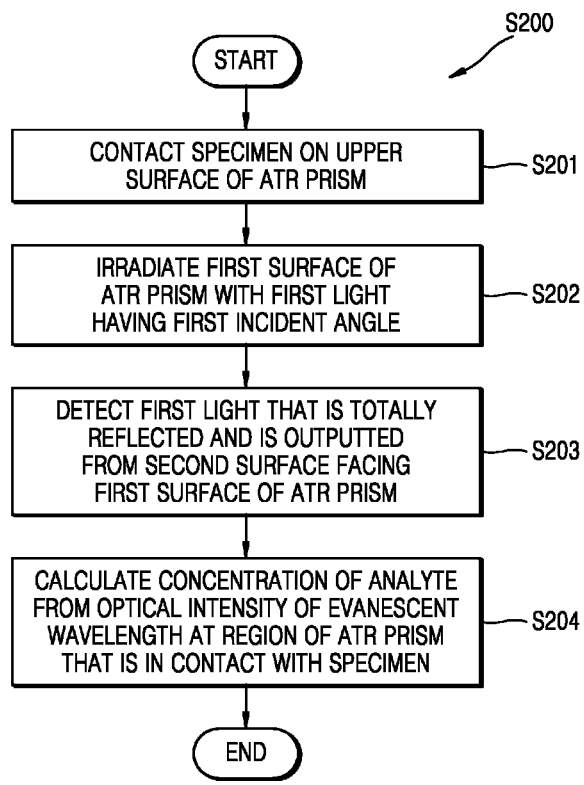
FIG. 6 is a flow chart explaining operation S200 of FIG. 5.

FIG. 6 is a flow chart of explaining operation S200 of FIG. 5.

Referring to FIG. 6, the specimen 160 is placed to contact the upper surface 131 of the ATR prism 130 at operation S201.

Next, a first light L1 is irradiated onto a slanted first surface 133 of the ATR prism 130 with a first incident angle at operation S202. The first incident angle may be greater than a first critical angle θc1 at which the first light L1 is totally reflected when the ATR prism 130 is in contact with air and a second critical angle θc2 at which the first light L1 is totally reflected when the ATR prism 130 is in contact with the specimen 160. All of the first light L1 is totally reflected at the first region A1 (refer to FIG. 3) and the second region A2 (refer to FIG. 3) of the ATR prism 130.

The first light L1 that is outputted by being totally reflected towards the second surface 134 opposite to the first surface 133 of the ATR prism 130 is detected in operation S203. The detected first light L1 may have an optical intensity that is attenuated by as much as an evanescent wave whose optical intensity is reduced by an analyte at the contact area of the specimen 160 with the ATR prism 130, at the original wavelength of the first light L1.

A concentration of the analyte from the optical intensity of the attenuated wavelength of the detected first light L1 at a region of the ATR prism 130 that is in contact with the specimen 160 is calculated in operation S204). The concentration of the analyte is calculated by the attenuated optical intensity. However, the concentration of the analyte may vary according to the contact area of the specimen 160 with the ATR prism 130.

Figure 7:
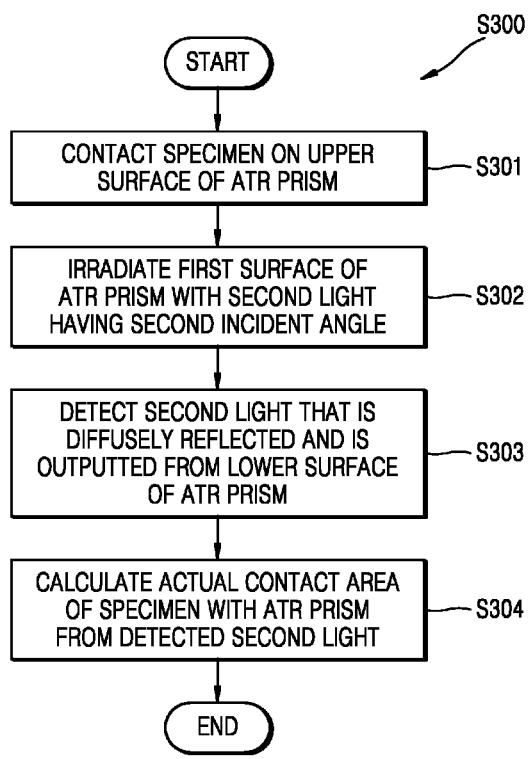
FIG. 7 is a flow chart explaining operation S300 of FIG. 5.

FIG. 7 is a flow chart of explaining operation S300 of FIG. 5.

Referring to FIG. 7, the specimen 160 is placed to contact the upper surface 131 of the ATR prism 130 in operation S301. The operation S301 may be the same as the operation S201, and thus, may not need to be performed again.

The second light L2 is inputted towards the slant first surface 133 of the ATR prism 130 with a second incident angle in operation S302. The second incident angle may be an angle between the first critical angle θc1, at which the second light L2 is totally reflected when the ATR prism 130 is in contact with air, and the second critical angle θc2, at which the second light L2 is totally reflected when the ATR prism 130 is in contact with the specimen 160. The second light L2 is diffusely reflected at the first region A1 (refer to FIG. 3) of the ATR prism 130 and is totally reflected at the second region A2 (refer to FIG. 3).

Next, the second light L2 that is outputted from the lower surface 132 of the ATR prism 130 by being diffusely reflected at the lower surface 132 is detected in operation S303.

The contact area A1 (refer to FIG. 3) between the ATR prism 130 and the specimen 160 is calculated from the detected second light L2 in operation S304. The contact area A1 is an actual contact area of the upper surface 131 of the ATR prism 130 with the specimen 160.

Next, a concentration of the analyte per unit area is calculated when the calculated concentration of the analyte is divided by the actual contact area of the specimen 160.

According to the exemplary embodiment, since a specimen contact area is directly measured by using an additional light source and a light receiver besides a light source and a light receiver for an ATR spectroscopic analysis, a concentration of an analyte that is corrected by using an actual contact area of a specimen with the ATR prism 130 may be measured.

Figure 8:
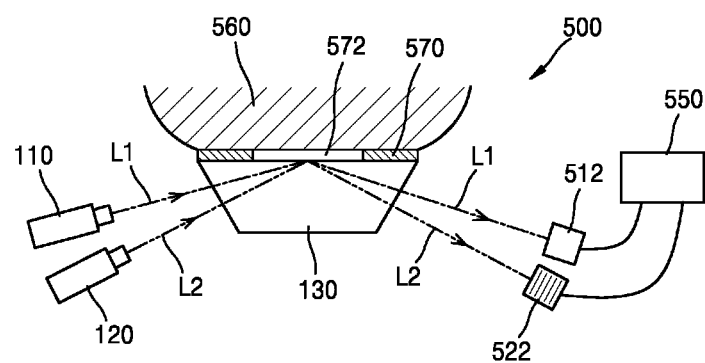
FIG. 8 is a schematic drawing of an ATR spectroscopic analysis apparatus having a device for measuring a specimen contact area, according to another exemplary embodiment.

FIG. 8 is a schematic drawing of an ATR spectroscopic analysis apparatus 500 having a device for measuring a specimen contact area, according to another exemplary embodiment. Like reference numerals are used to indicate elements that are substantially identical to the elements of FIG. 1, and thus, the detailed description thereof will not be repeated.

Referring to FIG. 8, the ATR spectroscopic analysis apparatus 500 includes a first light source 110 and a first light receiver 512 that are for ATR spectroscopic analysis, a second light source 120 and a second light receiver 522 that are for measuring a specimen contact area, and an ATR prism 130 (refer to FIG. 3) to which a first light L1 of the first light source 110 and a second light L2 of the second light source 120 enter. Also, the ATR spectroscopic analysis apparatus 500 includes a computation processing unit 550 (e.g., computation processor) that calculates a concentration of an analyte of a specimen 560 according to an actual specimen contact area in response to an electrical signal received from the first light receiver 512 and the second light receiver 522.

Figure 9:
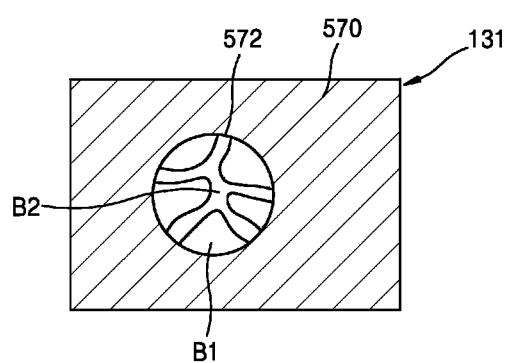
FIG. 9 is a mimic diagram showing a specimen that is in contact with an upper surface of an ATR prism in an opening of a mask.

FIG. 9 is a mimic diagram showing a specimen that is in contact with the upper surface 131 of the ATR prism 130 in an opening 572 of a mask 570.

Referring to FIGS. 8 and 9, the mask 570 having the opening 572 may be disposed on the upper surface 131 of the ATR prism 130. An area of the opening 572 may be a total area that includes a contact area B1 that is in contact with the specimen 560 and a contact area B2 that is in contact with air. The contact area B1 of the specimen 560 is determined when the air contact area B2 is subtracted from the area of the opening 572.

The mask 570 may be formed of a material that may generate a FTIR with respect to the first light L1 and the second light L2. That is, a third critical angle $\theta c3$ is greater than the first critical angle $\theta c1$ and the second critical angle $\theta c2$. The third critical angle $\theta c3$ is an angle at which light that has passed through the ATR prism 130 is totally reflected at a surface of the ATR prism 130 that is in contact with the mask 570. Referring to FIG. 4, the mask 570 may be formed of a material that generates a FTIR at a first incident angle of the first light L1 and the second incident angle of the second light L2. That is, the first light L1 and the second light L2 that are irradiated onto the ATR prism 130 should not be outputted from the second surface 134 of the ATR prism 130. In order for the third critical angle $\theta c3$ to be greater than the first critical angle $\theta c1$ and the second critical angle $\theta c2$, the mask 570 may have a refractive index greater than that of air and a living body. For example, the mask 570 may be formed of silicon (Si), germanium (Ge), or tungsten (W), which have a refractive index greater than 2.6 at a wavelength range from about 500 nm to about 1,400 nm.

The first light source 110 may be a device that emits infrared rays. The first light source 110 may be a light-emitting device or a laser diode that emits the first light L1 having a wavelength in a range from about 1,000 nm to about 1,500 nm. The first light source 110 irradiates the first surface 133 of the ATR prism 130 with the first light L1 having a first incident angle. The first incident angle is greater than the first critical angle $\theta c1$ and the second critical angle $\theta c2$, and accordingly, the first light L1 is totally reflected when the first light L1 is inputted onto the opening 572 of the mask 570. However, when the first light L1 is inputted onto the mask 570 surrounding the opening 572 of the mask 570, the first light L1 is diffusely reflected, and accordingly, is not inputted onto the first light receiver 512.

The first light receiver 512 may be a photodiode that detects the first light L1. The first light receiver 512 generates an electrical signal in response to a first output light that is from the first light L1 that is emitted from the first light source 110 and is totally reflected at the ATR prism 130, and is outputted from the slant second surface 134 of the ATR prism 130. The electrical signal detected by the first light receiver 512 is transmitted to the computation processing unit 550. The computation processing unit 550 compares the electrical signal with a wavelength spectrum of the first input light, and calculates a concentration of an analyte by computing an attenuated wavelength and its intensity in a wavelength spectrum of the first output light. This result of calculation is an analysis result of the specimen 560 at the actual contact area B2 of the specimen 560 that is actually in contact with the upper surface 131 of the ATR prism 130.

The second light source 120 may emit the second light L2 having a wavelength in a range from about 400 nm to about 750 nm. The second light source 120 may be a light-emitting device or a laser diode. The second light source 120 may be a red light source by using a heat generating material, such as tungsten. The second light source 120 irradiates the first surface 133 of the ATR prism 130 with the second light L2 having a second incident angle. The second incident angle may be an angle between the first critical angle $\theta c1$ and the second critical angle $\theta c2$. Accordingly, the second light L2 is totally reflected at a region of the first surface 133 that contacts air and is diffusely reflected at a region of the first surface 133 that contacts the specimen 560.

However, when the second light L2 is irradiated onto the mask 570 by deviating from the opening 572 of the mask 570, the second light L2 is diffusely reflected, and accordingly, is not received by the second light receiver 522.

The second light receiver 522 may be disposed to detect the second light L2 outputted from the second surface 134 of the ATR prism 130. The second light receiver 522 may be an imaging device. For example, the second light receiver 522 may be a photodiode array or a CCD.

The second light receiver 522 detects the second light L2 that is totally reflected at the ATR prism 130 and is outputted towards the second surface 134 of the ATR prism 130. The second light receiver 522 generates an electrical signal in response to the second output light and transmits the electrical signal to the computation processing unit 550. The computation processing unit 550 generates a wavelength spectrum with respect to the contact area B2 at an interface between air and the ATR prism 130 according to the electrical signal by the second light receiver 522. According to the wavelength spectrum, an actual contact area of the specimen 560 with air in the opening 572 of the mask 570 is calculated. The second light receiver 522 calculates a reverse image of the actual contact area of the specimen 560. When the air contact area B2 is subtracted from the opening area of the specimen 560, the actual contact area B1 of the specimen 560 in contact with the upper surface 131 of the ATR prism 130 in the opening 572 of the mask 570 is calculated.

Accordingly, a concentration of an analyte per unit area of the specimen 560 is obtained when the resultant data of the analyte measured at the first light receiver 512 is divided by the actual contact area.

In the current exemplary embodiment, the first light receiver 512 is separately installed from the second light receiver 522. However, the current exemplary embodiment is not limited thereto. For example, only a single light receiver may be used. If the first light L1 and the second light L2 have different wavelengths, the first light L1 and the second light L2 may be separately detected by using the single light receiver.

Figure 10:
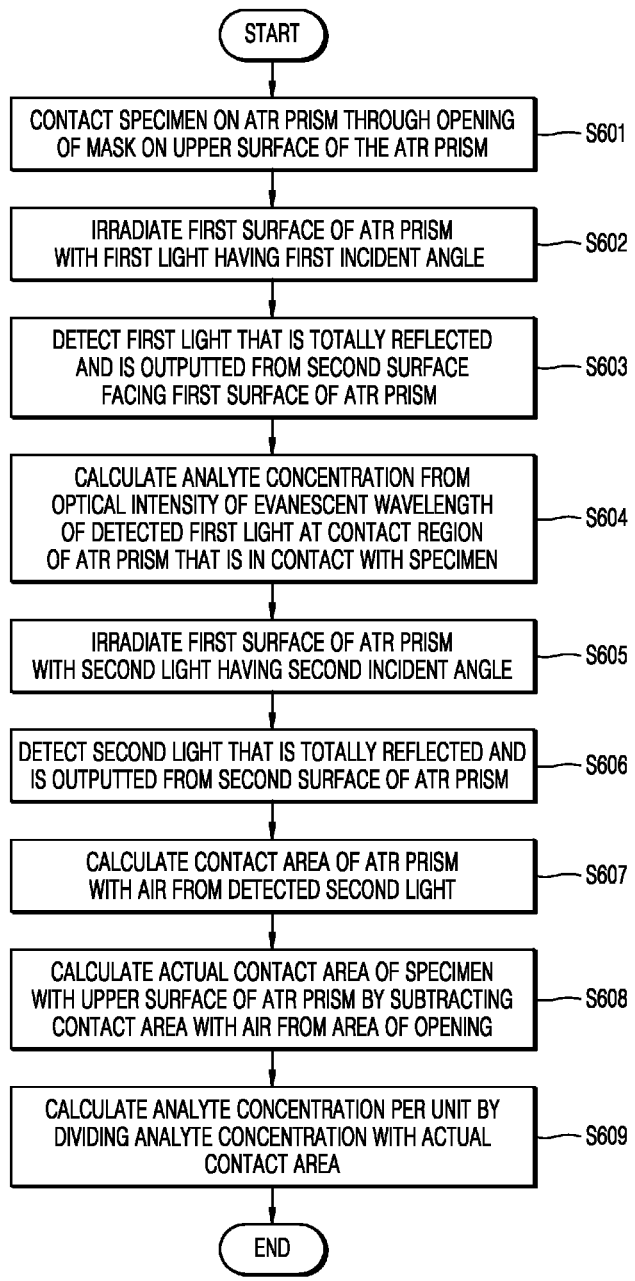
FIG. 10 is a flow chart illustrating a method of operating an ATR spectroscopic analysis apparatus according to another exemplary embodiment.

FIG. 10 is a flow chart illustrating a method of operating an ATR spectroscopic analysis apparatus according to another exemplary embodiment.

The specimen 560 is placed to contact the upper surface 131 of the ATR prism 130 through the opening 572 formed in the mask 570 in operation S601.

Next, the slanted first surface 133 of the ATR prism 130 is irradiated with the first light L1 having a first incident angle in operation S602. The first incident angle may be greater than the first critical angle θc1 at which the first light L1 is totally reflected when the ATR prism 130 is in contact with air and the second critical angle θc2 at which the first light L1 is totally reflected when the ATR prism 130 is in contact with the specimen 560. The first light L1 is totally reflected at the both first region B1 and the second region B2 in the opening 570 on the ATR prism 130. The first light L1 that is irradiated onto the mask 570 surrounding the opening 572 is diffusely reflected.

Next, the first light L1 is detected after being totally reflected at the opening 572 of the mask 570 and being outputted towards the second surface 134 facing the first surface 133 of the ATR prism 130 in operation S603. [98] A concentration of the analyte is calculated from the optical intensity of the evanescent wavelength of the detected first light L1 whose optical intensity is reduced at the contact region B1 of the specimen 560 with the upper surface 131 of the ATR prism 130 in operation S604. The concentration of the analyte is calculated by the attenuated optical intensity. However, the concentration of the analyte may vary according to the contact area of the specimen 560.

Next, the second light L2 is irradiated onto the slant first surface 133 of the ATR prism 130 with a second incident angle in operation S605). The second incident angle may be an angle between the first critical angle θc1 at which the first light L1 is totally reflected when the ATR prism 130 is in contact with air and the second critical angle θc2 at which the first light L1 is totally reflected when the ATR prism 130 is in contact with the specimen 560. The second light L2 is diffusely reflected at the first region B1 of the ATR prism 130, and is totally reflected at the second region B2. The first light L1 that is irradiated onto the mask 570 surrounding the opening 572 is diffusely reflected.

Next, the second light L2 that is totally reflected and outputted towards the second surface 134 of the ATR prism 130 is detected in operation S606.

Next, the contact area of the ATR prism 130 with air from the second light L2 is calculated in operation S607.

Next, the contact area B1 between the specimen 560 and the ATR prism 130 in the opening 572 is calculated by subtracting the contact area with air from the opening area in operation S608.

Next, a concentration of the analyte per unit is calculated by dividing the concentration of the analyte obtained in the operation S604 with the contact area B1 of the specimen 560 in operation S609.

In the exemplary embodiment described above, the first light L1 and the second light L2 respectively have different wavelengths. However, the current exemplary embodiment is not limited thereto. For example, according to other exemplary embodiments, a light source may emit the first light L1 and the second light L2 such that the first light L1 and the second light L2 have the same wavelength but the first light L1 may have a first incident angle, the second light L2 may have a second incident angle, and the first light L1 and the second light L2 may be respectively irradiated with different timings from each other.

According to an exemplary embodiment, after forming a mask having an opening on the ATR prism, a region of a specimen that is in contact with the ATR prism is measured in the opening. Thus, although the contact area varies, a concentration of an analyte per unit area may be measured by dividing the measured concentration of the analyte with the contact area.

While one or more exemplary embodiments have been described with reference to the figures, it will be understood by those of ordinary skill in the art that various changes in form and details may be made therein without departing from the spirit and scope as defined by the following claims.

What is claimed is:

1. An attenuated total reflection (ATR) spectroscopic analysis apparatus comprising:
   an ATR prism comprising:
      an upper surface that contacts a specimen,
      a lower surface facing the upper surface,
      a first surface that is slanted and connected to the upper surface and the lower surface, and
      a second surface that is slanted and connected to the upper surface and the lower surface and facing the first surface;
   a light source configured to emit a light towards the first surface of the ATR prism;
   a light receiver that is provided to face the lower surface of the ATR prism and configured to receive the light that is diffusely reflected and output from the lower surface and output an electrical signal based on the received light; and
   a computation processor configured to calculate a contact area of the specimen with the upper surface of the ATR prism in response to the electrical signal received by the light receiver.

2. The ATR spectroscopic analysis apparatus of claim 1, further comprising:
   another light source configured to emit another light towards the first surface of the ATR prism; and
   another light receiver configured to receive the other light that is totally internally reflected, passed through the ATR prism, and output from the second surface and output an electrical signal based on the received light;
   wherein the computation processor is configured to calculate an analyte concentration of the specimen by using the electrical signal received by the another light receiver, and calculate an analyte concentration of the specimen per unit area by dividing the calculated analyte concentration with the contact area of the specimen with the ATR prism.

3. The ATR spectroscopic analysis apparatus of claim 2, wherein the light source is a light-emitting device or a laser diode configured to emit the light having a shorter wavelength than a wavelength of the another light.

4. The ATR spectroscopic analysis apparatus of claim 1, wherein the light receiver is configured to calculate an image according to the contact area of the specimen that is in contact with the upper surface of the ATR prism by receiving the light.

5. The ATR spectroscopic analysis apparatus of claim 4, wherein the light receiver is a photodiode array or a charge-coupled device (CCD).

6. An ATR spectroscopic analysis apparatus comprising:
   an ATR prism comprising:
      an upper surface that contacts a specimen,
      a lower surface facing the upper surface,
      a first surface that is slanted and connected to the upper surface and the lower surface, and
      a second surface that is slanted and connected to the upper surface and the lower surface and facing the first surface;
   a mask that is provided on the upper surface of the ATR prism and has an opening;
   a light source configured to emit a light towards the first surface of the ATR prism;
   a light receiver configured to receive the light that is output from the second surface by being totally internally reflected and passed through the ATR prism and output an electrical signal based on the received light; and
   a computation processor configured to calculate a contact area of the specimen with the upper surface of the ATR prism in the opening of the mask in response to the electrical signal received from the light receiver.

7. The ATR spectroscopic analysis apparatus of claim 6, further comprising:
   another light source configured to emit another light towards the first surface of the ATR prism; and
   another light receiver configured to receive the first light that is totally internally reflected, passed through the ATR prism, and output from the second surface and output an electrical signal based on the received light;
   wherein the computation processor is configured to calculate an analyte concentration of the specimen by using the electrical signal received from the another light receiver, calculate an area of a first region of the ATR prism that is in contact with air in the opening by using the electrical signal received by the light receiver and calculate the contact area of the specimen in the opening by subtracting the area of the first region from the area of the opening, and calculate an analyte concentration of the specimen per unit area by dividing the analyte concentration with the contact area.

8. The ATR spectroscopic analysis apparatus of claim 7, wherein the light source is configured to emit light having a shorter wavelength than a wavelength of the another light.

9. The ATR spectroscopic analysis apparatus of claim 6, wherein the light receiver is configured to calculate a reverse image of the contact area of the specimen by receiving the second light.

10. The ATR spectroscopic analysis apparatus of claim 9, wherein the light receiver is a photodiode array or a charge-coupled device (CCD).

11. The ATR spectroscopic analysis apparatus of claim 6, wherein the mask is formed of germanium (Ge), silicon (Si), or tungsten (W).

12. A method of operating an attenuated total reflection (ATR) spectroscopic analysis apparatus, the method comprising:
   measuring an analyte concentration of a specimen that is in contact with a surface of an ATR prism;
   calculating a contact area of the specimen with the ATR prism; and
   calculating an analyte concentration per unit area by correcting the analyte concentration with the contact area of the specimen.

13. The method of claim 12, wherein the measuring of the analyte concentration comprises:
   contacting the specimen on the surface of the ATR prism, the surface being an upper surface;
   emitting a first light with a first incident angle towards a slanted first surface of the ATR prism, the slanted first surface being connected to the upper surface;
   detecting the first light that is totally internally reflected and output from a slanted second surface facing the slanted first surface of the ATR prism, the slanted second surface being connected to the upper surface; and
   calculating the analyte concentration based on an optical intensity of an evanescent wavelength of the detected first light at a region of the ATR prism that is in contact with the specimen.

14. The method of claim 13, wherein the first incident angle is greater than a first critical angle at which the first light is totally internally reflected at a region of the ATR prism that is in contact with air and a second critical angle at which the first light is totally internally reflected at a region of the ATR prism that is in contact with the specimen.

15. The method of claim 14, wherein the calculating of the contact area of the specimen comprises:
   contacting the specimen on the upper surface of the ATR prism;
   emitting a second light with a second incident angle towards the slanted first surface of the ATR prism;
   detecting the second light that is diffusely reflected and is output from a lower surface of the ATR prism facing the upper surface; and
   calculating the contact area of the specimen that is in contact with the ATR prism based on the detected second light.

16. The method of claim 15, wherein the second incident angle is an angle between the first critical angle and the second critical angle.

17. The method of claim 14, wherein the calculating of the contact area of the specimen comprises:
   contacting the specimen with the upper surface of the ART prism through an opening of a mask formed on the upper surface of the ATR prism;
   emitting the second light with a second incident angle towards the slanted first surface of the ATR prism;
   detecting the second light that is totally internally reflected and is output from the slanted second surface;
   calculating a contact area of the ATR prism that is in contact with air based on the detected second light; and
   calculating the contact area of the specimen that is in contact with the upper surface of the ATR prism in the opening by subtracting the contact area with air from an area of the opening.

18. The method of claim 17, wherein the second incident angle is an angle between the first critical angle and the second critical angle.

19. The method of claim 18, wherein a total internal reflection critical angle of the mask is greater than the first critical angle and the second critical angle, and the first light and the second light generate a frustrated total internal reflection (FTIR) at an interface between the ATR prism and the mask.

20. The method of claim 18, wherein the mask is formed of germanium (Ge), silicon (Si), or tungsten (W).

\* \* \* \* \*